(12) United States Patent
Joseph et al.

(10) Patent No.: US 8,552,383 B2
(45) Date of Patent: Oct. 8, 2013

(54) METHODS AND SYSTEMS FOR IN-VITRO ANALYSIS OF BIOLOGICAL CELLS AND/OR MICROORGANISMS

(75) Inventors: Heinz Walter Joseph, Freiburg (DE); Nicolas Lembert, Reutlingen (DE)

(73) Assignee: Tetec Tissue Engineering Technologies AG, Reutlingen (DE)

( * ) Notice: Subject to any disclaimer, the term of this patent is extended or adjusted under 35 U.S.C. 154(b) by 0 days.

(21) Appl. No.: 12/560,290

(22) Filed: Sep. 15, 2009

(65) Prior Publication Data

US 2011/0062338 A1 Mar. 17, 2011

(51) Int. Cl.
*A61B 6/00* (2006.01)

(52) U.S. Cl.
USPC .................................................... 250/339.09

(58) Field of Classification Search
USPC ............................ 250/339.08; 435/4; 702/19
See application file for complete search history.

(56) References Cited

U.S. PATENT DOCUMENTS

| | | | |
|---|---|---|---|
| 6,054,262 A | 4/2000 | Hayakawa et al. | |
| 6,274,871 B1 | 8/2001 | Dukor et al. | |
| 6,493,080 B1 | 12/2002 | Boese | |
| 6,620,621 B1 * | 9/2003 | Cohenford et al. | 436/63 |
| 8,195,402 B2 | 6/2012 | Joseph | |
| 2005/0123917 A1 | 6/2005 | Labischinski et al. | |
| 2006/0223050 A1 | 10/2006 | Crowe et al. | |
| 2007/0003921 A1 | 1/2007 | Andrus | |
| 2008/0132418 A1 * | 6/2008 | Ismail et al. | 506/6 |

FOREIGN PATENT DOCUMENTS

| | | |
|---|---|---|
| DE | 199 49 953 A1 | 5/2001 |
| DE | 199 40 981 C1 | 7/2001 |
| DE | 100 60 560 A1 | 12/2001 |
| DE | 101 62 205 A1 | 7/2003 |
| DE | 101 62 960 A1 | 7/2003 |
| DE | 102 20 368 A1 | 12/2003 |
| DE | 102 22 896 A1 | 12/2003 |
| WO | WO 02/33400 A1 | 4/2002 |

OTHER PUBLICATIONS

Ami, D., et al., "Embryonic stem cell differentiation studied by FT-IR spectroscopy," *Biochim. Biophys. Acta* 1783:98-106, Elsevier Science Publishers, The Netherlands (2008).

Erukhimovitch, V., "Spectroscopic characterization of human and mouse primary cells, cell lines and malignant cells", *Photochem. Photobiol.* 76:446-51, American Society for Photobiology, United States (2002).

(Continued)

*Primary Examiner* — Marcus Taningco
(74) *Attorney, Agent, or Firm* — Sterne, Kessler, Goldstein & Fox P.L.L.C.

(57) ABSTRACT

Methods for in-vitro analysis of biological cells and/or microorganisms to determine characteristics such as: degree of differentiation, cell type, donor individuals, culture conditions, purity, lack of natural characteristic, or additional characteristics in comparison to natural characteristics. The methods include the steps of: (a) projecting infrared radiation on a sample; (b) recording spectral characteristics of the sample; (c) deriving a Fourier transform infrared spectrum (FT-IR) from the collected spectral characteristics; (d) generating a derivative transformation of the FT-IR spectrum; (e) comparing said derivative transformation with a derivative of a reference FT-IR spectrum; (f) identifying deviations of said derivative from said reference derivative; and (g) providing an analysis of said characteristics based on the presence of said deviations. In addition, the invention relates to an apparatus for carrying out the disclosed methods.

8 Claims, 3 Drawing Sheets

(56) References Cited

OTHER PUBLICATIONS

Guë, M., et al., "Bacterial Swarming: A Biochemical Time-Resolved FTIR-ATR Study of *Proteus mirabilis* Swarm-Cell Differentiation," *Biochem.* 40:11938-11945, American Chemical Society, United States (2001).

Oberreuter, et al., "Quantification of micro-organisms in binary mixed populations by Fourier transform infrared (FT-IR) spectroscopy," *Lett. Appl. Microbiol.* 30:85-89, Published for the Society for Applied Bacteriology by Blackwell Scientific Publications, United Kingdom (2000).

Extended European Search Report for European Application No. EP 09 17 0329, filed on Jan. 12, 2009, European Patent Office, Germany.

English language Abstract of European Patent Publication No. DE 199 49 953 A1, EPO, espacenet database-worldwide (2001).

English language Abstract of European Patent Publication No. DE 199 40 981 C1, EPO, espacenet database-worldwide (2001).

English language Abstract of European Patent Publication No. DE 100 60 560 A1, EPO, espacenet database-worldwide (2001).

English language Abstract of European Patent Publication No. DE 101 62 205 A1, EPO, espacenet database-worldwide (2003).

English language Abstract of European Patent Publication No. DE 101 62 960 A1, EPO, espacenet database-worldwide (2003).

English language Abstract of European Patent Publication No. DE 102 20 368 A1, EPO, espacenet database-worldwide (2003).

English language Abstract of European Patent Publication No. DE 102 22 896 A1, EPO, espacenet database-worldwide (2003).

Office Action mailed on Aug. 24, 2007, in U.S. Appl. No. 10/888,411, Joseph, filed Jul. 9, 2004.

Office Action mailed on May 14, 2008, in U.S. Appl. No. 10/888,411, Joseph, filed Jul. 9, 2004.

Advisory Action mailed on Sep. 24, 2008, in U.S. Appl. No. 10/888,411, Joseph, filed Jul. 9, 2004.

Office Action mailed on Feb. 17, 2009, in U.S. Appl. No. 10/888,411, Joseph, filed Jul. 9, 2004.

Office Action mailed on Dec. 7, 2009, in U.S. Appl. No. 10/888,411, Joseph, filed Jul. 9, 2004.

Office Action mailed on Jun. 21, 2011, in U.S. Appl. No. 10/888,411, Joseph, filed Jul. 9, 2004.

Advisory Action mailed on Sep. 14, 2011, in U.S. Appl. No. 10/888,411, Joseph, filed Jul. 9, 2004.

Office Action mailed on Dec. 20, 2011, in U.S. Appl. No. 10/888,411, Joseph, filed Jul. 9, 2004.

Notice of Allowance mailed on Mar. 1, 2012, in U.S. Appl. No. 10/888,411, Joseph, filed Jul. 9, 2004.

\* cited by examiner

METHODS AND SYSTEMS FOR IN-VITRO ANALYSIS OF BIOLOGICAL CELLS AND/OR MICROORGANISMS

CROSS-REFERENCE TO RELATED APPLICATION

U.S. patent application Ser. No. 10/888,411, filed Jul. 9, 2004, which published as U.S. Patent Application Publication No. 2006/0008795, is herein incorporated by reference in its entirety.

BACKGROUND OF THE INVENTION

1. Field of the Invention

The present invention relates generally to infrared (IR) spectroscopy systems and methods for in-vitro analysis of biological cells and/or microorganisms. More particularly, the systems and methods of the present invention allow specific and quick analysis of degree of differentiation, cell types, donor individuals, culture conditions, purity, lack of natural characteristic, or additional characteristics in comparison to natural characteristic.

2. Background Art

In the past decade application of different suitable medical and non-medical techniques have greatly advanced areas of clinical study. It is well known that the ease of medical treatment depends greatly on the speed of a diagnosis. Thus, the sensitivity and precise discriminatory nature of early diagnostic methods are very important in the effective medical treatment of patients. The potential of techniques for screening and disease diagnosis in clinical settings, as well as in the medical area regarding transplants, has been already investigated by various research groups. A number of these techniques have been applied in recent years to study different biological objects such as biological fluids and tissues. Many of these techniques are aimed specifically to identify a certain pathological conditions or to determine, differentiate and typify different biological cells or microorganisms.

Until now, the most conventional method for controlling, identifying, typifying, quantifying, classifying and monitoring biological objects, such as different types of biological cells and microorganisms as well as starting materials and the finished products used for example in the transplantation medicine, is the Polymerase Chain Reaction (PCR) technique. For an emerging gene-based identification method, genus-specific or species-specific PCR primers or nucleotide probes are applied to an object of interest. However, there are some limitations to the use of PCR such as (i) greater expense than starting PCR as twice as much enzyme and reagents are used, (ii) extra manipulations and length of the assay as cycling blocks cannot be programmed for all cycles from the start, and (iii) applies only to short DNA fragments. Further, such determinations are very time-consuming and require sophisticated apparatuses to carry out the different tests.

A further concept is the use of cell type specific markers. In this respect it is very difficult to find cell type specific markers addressed only to one specific cell type. This concept has the problem that only quantities in expression can be determined but no answer is given whether a different type of cell is present or not.

Other standard methods to read out biological systems, in particular cells or microorganisms, are for example fluores cent and chemiluminescent-imaging techniques as well as NMR spectroscopy:

(i) Fluorescent and chemiluminescent-imaging methods require labeling of a component by a marker and usually only detect the concentration of the marker molecule.

(ii) Although solution NMR-spectroscopy provides a detailed image of the structure of a bio-object, the NMR method is much more complex. Furthermore, for the NMR analysis the large quantities of the samples are needed which have to be further labeled by isotopes of carbon ($^{13}C$), nitrogen ($^{15}N$), oxygen ($^{17}O$), and hydrogen ($^{2}H$).

Infrared (IR) spectroscopy is a technique routinely used by chemists, biochemists, and material scientists as a standard analyzing method. The observed spectroscopic signals are due to the absorption of infrared radiation that is specific to functional groups of the molecule. These absorption frequencies are associated with the vibrational motions of the nuclei of a functional group and show distinct changes when the chemical environment of the functional group is modified. Infrared spectroscopy essentially provides a molecular fingerprint and has thus always the potential as a diagnostic and monitoring tool in biology and medicine. Infrared spectra contain a wealth of information on the molecule, in particular they are used for the identification and quantification of molecular species, the interactions between neighboring molecules, their state of hydration, their overall shape, etc. Infrared spectra can be used as a sensitive marker of structural changes of cells and of reorganization occurring in cells. The diagnostic potential of infrared spectroscopy is being realized in many medical research programs based on the fundamental premise that in any pathologic process, the chemical change must precede the morphological or symptomatic manifestation. Organic applications of IR spectroscopy are almost entirely concerned with frequencies in the range of 400-4000 $cm^{-1}$ (mid-infrared). Frequencies lower than 400 $cm^{-1}$ are called far-infrared and those greater than 4000 $cm^{-1}$ are called near-infrared.

Thus, there are several important advantages in using this technique: results are obtained relatively quickly with less labor input than many other techniques. The use of IR spectroscopy may provide more precise information on the exact nature of, for example, a disease based on sampling of a biological fluid or tissue. The method also allows to monitor the dynamics of the characteristic change, which is important in determining the exact stage of a biological object, such as cells or microorganisms, or of a disease.

Erukhimovitch et al. (*Photochemistry and Photobiology*, 2002, 76(4), 446-451) discloses a method for the diagnosis and characterization of cell and tissue pathology. In particular, Erukhimovitch et al. discloses the use of Fourier Transform Infrared (FT-IR) microspectroscopy instead of conventional FT-IR spectroscopy as having advantages in the diagnostic of malignancies. For this purpose FT-IR microspectra of two types of retrovirus-transformed malignant cells were compared with those of non-transformed primary cells and with those of two types of cell lines. Erukhimovitch et al. suggests using, for example, a band corresponding to the $PO_2^-$ symmetric stretching mode to control the levels of phosphate and other metabolites. Erukhimovitch et al. discloses the use of FT-IR microspectroscopy for the investigation of the metabolism in mouse and human cells by comparing the FT-IR microspectra of two types of retrovirus-transformed malignant cells with those of non-transformed primary cells and with those of two types of cell lines. Thus, Erukhimovitch et al. is directed to study of a metabolism of cells which can be considered as an instanta neous image of the cell status and can be further used for classification of the cell metabolic activity and cell metabolic status.

However, the principal problem in FT-IR microspectroscopy is the presence of scattered light due to diffraction which limits the spatial resolution by increasing the noise. Diffraction is significant when the aperture dimensions approach the wavelength of the IR radiation. The main effect of diffraction is that at small aperture sizes, light spreads outside the specified area into the surrounding region. As higher spatial resolution is sought, the problem increases, as the apertures are smaller, ultimately leading to loss of spectral quality and photometric accuracy. Therefore, the spectrum obtained does not always correspond exactly to the area that is observed visually and defined by the remote aperture. This is especially true when the sample dimensions are very small. Furthermore, any time that measurements are made when the size of the sample that is being observed is equal to, or slightly greater than, the diffraction limit, some radiation is transmitted to the detector from outside the region that was selected by the remote aperture.

Oberreuter et al. (*Letters in Applied Microbiology*, 2000, 30, 85-89) discloses FT-IR determination of the ratios of different microorganisms in mixtures comprising a two-component food-associated yeast system and a two-component yoghurt lactic acid bacteria system. In particular, Oberreuter et al. suggests to use FT-IR spectroscopy for the evaluation of the calibration curves of single components and a mixture comprising *Saccharomyces cerevisiae* and *Hanseni-aspora uvarum* as well as a mixture comprising *Lactobacillus acidophilus* and *Streptococcus salivarius*, which can be further used for the quantification of these microorganisms in a mixture. Oberreuter et al. uses FT-IR spectroscopy for differentiation between individual species present in a mixed population.

Methods for the determination, especially typification and status check of well or fully differentiated mammalian cells are required especially in the field of transplantation medicine. For example, it is possible to produce replacement tissue by taking intact cells of the suitable tissue type from the transplant recipient, cultivating them in-vitro and re-introducing them into the patient after the necessary cell count has been reached. This can be effected either in the form of solutions or cultivated tissue portions or by cultivating the cells on a matrix (which preferably may be absorbed biologically) and re-implanting them together with the matrix. For example, suitable methods, matrices and cultivation media are described in the German applications 101 62 205.8, 101 62 960.5, 102 20 368.7, 102 22 896.5 (corresponds to AU 2003240618 A1) and the literature cited therein.

DE 103 26 966 A1 and its equivalent US 2006/0008795 A1 refers to a method for the in-vitro determination, especially typification, of well of fully differentiated mammal cells using Infrared Spectroscopy, especially their Fourier transformation (FT-IR). In particular, DE 103 26 966 A1 discloses the use of FT-IR spectroscopy for differentiation between well and fully differentiated cells of one specific species.

IR spectroscopy methods suggested in the prior art have similar limitations: they allow for selective determination or identification only of some biological objects such as bacteria, yeast or mammal cells.

Especially in the field of tissue engineering, transplant medicine as well as in questions of regulatory affairs and drug safety of in-vitro cultured cells and/or microorganisms there is a need to assure the quality, purity and origin of biological cells and/or microorganisms.

There is a need for a universal technique that would allow for a quick, broad examination of various biological objects such as biological cells and/or microorganisms as well as for distinguishing their characteristics.

BRIEF SUMMARY OF THE INVENTION

It is therefore an object of the present invention to provide a quick and non-destructive method for analysis of biological cells and/or microorganisms characteristics, which avoids the disadvantages of the prior art.

Presented herein are methods for in-vitro analysis of biological cells and/or microorganisms to determine characteristics such as: degree of differentiation, cell type, donor individuals, culture conditions, purity, lack of natural characteristic, and/or additional characteristics in comparison to natural characteristics. The methods includes the steps of: (a) projecting infrared radiation on a sample of biological cells and/or microorganisms, said radiation including a selected number of wavelengths; (b) recording the spectral characteristics after interaction with said sample; (c) deriving a Fourier transform infrared spectrum (FT-IR) from the collected spectral characteristics; (d) generating a first or multiple derivative transformation of the FT-IR spectrum suitable for analysis in a computer; (e) comparing said derivative transformation of the FT-IR spectrum with a derivative of a reference FT-IR spectrum; (f) identifying deviations of said derivative transformation of the FT-IR spectrum from said derivative of a reference FT-IR spectrum; and (g) providing an analysis of said characteristics based on the presence of said deviations. In addition, the invention relates to an apparatus for carrying out the herein described methods. Such methods are particularly applicable to the fields of transplantation/graft and tissue engineering, clinical medicine, pharmaceutical industry, quality control and/or drug safety.

DETAILED DESCRIPTION OF THE INVENTION

It has surprisingly been found that the objects of the invention can be achieved by the use of the infrared spectroscopy. The infrared irradiation of a sample, such as biological cells and/or microorganisms, results in a spectrum of a higher complexity. Because the IR beam is directed towards all components of a sample, e.g., cellular or non-cellular, the final spectrum represents the average spectra of all components of the sample. In order to identify structural or chemical changes of a biological sample, the method according to the present invention especially provides the Fourier transformation of the obtained spectra and their following derivatization that increases significantly the sensitivity and reliability of IR spectral analysis of the biological objects such as biological cells and/or microorganisms.

One advantage of the method of the present invention is in utilization of a newly discovered fact that specific type of biological cells and/or microorganisms have particular and distinct ranges of frequency in which IR absorbance spectra change. Therefore, once a change or deviation from an established norm is detected, the range of frequency where the structural change has occurred identifies a specific cell and/or microorganism.

It has therefore unexpectedly been found that the method according to the present invention has improved characteristics compared to known methods, even when using the same spectroscopic technique. The method for in-vitro analysis of biological cells and/or microorganisms according to the present invention avoids chemical alteration or physical separation of the components of the biological sample.

According to the invention the term "analysis" means examination, determination, classification, identification, typification, differentiation, distinguishing, monitoring, quantification and/or diagnosis of a biological sample.

The term "donor individual" refers to living organisms, preferably to a mammal, providing cells originated from an organ or other biological tissue or blood for analysis. This term also refers to the distinction of the donor individual based on specific structural information contained in biological cells.

The term "differentiation" refers to a cellular differentiation wherein a less specialized cell becomes a more specialized cell type.

The term "degree of differentiation" refers to a ratio between well or fully differentiated cells and unchanged (un-differentiated) cells.

The term "characteristic" refers to biological properties of biological cells and/or microorganisms and is based on structural and/or chemical information contained in these cells and/or microorganisms.

The term "natural characteristics" refers to an original (un-changed) state of a biological cell and/or microorganism. This term further refers to a function of a cell and/or microorganism to specify/typify itself during the time or under applied conditions.

The term "lack of natural characteristic" refers to a natural characteristic of an analyzed biological object which shows lack of some original characteristics. By way of example, an insulin-producing cell that has lost its ability to produce insulin would be an example of a cell that has a lack of natural characteristic.

The term "additional characteristic in comparison to natural characteristic" refers to natural characteristic of an analyzed biological object which shows an additional characteristic in comparison to natural/original characteristics.

The term "culture conditions" refers to a composition of a medium having specific properties wherein the biological cells and/or microorganisms are cultured. Further, this term refers to combined influence of environmental conditions, e.g., temperature, light intensity, humidity, and presence of some specific substances, e.g., electrolytes, organic or inorganic molecules, inhibitors, etc., which can significantly influence the growth and/or modification of biological objects such as biological cells and/or microorganisms. As an example, the term also comprises specific serum concentration of the culture medium, e.g. 5% or 10% serum.

The term "purity" refers to materials meeting the purity requirements of chemical products admitted in the pharmaceutical sector, for biological/biochemical research and analysis. Further, in the field of transplant/graft medicine and tissue engineering the term "purity" refers to the pureness of the transplant/graft meaning that the cells of the transplant/graft are not infected by any detrimental bacteria or virus and are not contaminated by cells of undesired tissue or donor individuals. The critical parameters involved are absence of inhibitors such as traces of heavy metals, enzymes or other biological objects like bacteria and viruses that could interfere in the analysis, as well as some dehydrated culture media auxiliary agents. In addition, the term "purity" refers to a degree of pureness required in quality control of transplants, blood products and pharmaceutical drugs and/or pharmaceutical products concerning regulatory affairs as well as drug safety. In this respect almost each country has its own act which provides the respective governmental requirements.

The term "cell type" refers to a distinct morphological or functional form of a cell, e.g., to a differentiated cell, which may be fully or well differentiated or non-differentiated.

The method of the invention permits analysis of biological cells and/or microorganisms—in a simple and reliable manner by irradiating the cells or an aliquot thereof with infrared light and recording the absorption spectrum obtained, carrying out a Fourier transformation on this absorption spectrum in order to obtain an FT-IR spectrum, calculating the first derivative and/or multiple (higher) derivative(s) of the FT-IR spectrum and comparing said derivative(s) in a preselected wave number range with one or more derivative(s) of the same order of reference FT-IR spectra obtained earlier. The reference FT-IR spectra or earlier determined spectra, acquired under the same experimental spectroscopic conditions as the sample spectra, are generally obtained starting from preparations of purified sample, which preferably is the desired biological cell type or microorganism or defined mixture thereof or with other defined components. In case of cartilage transplants, for example, reference FT-IR spectra are obtained from purified preparations of chondrocytes. The derivatives of the FT-IR spectra of the transplant to be determined are then compared with the derivatives of this reference FT-IR spectrum.

The spectra derivatives, especially the second derivative of the original spectra, offers a direct way to identify the peak frequencies of characteristic components and thus permits much more detailed qualitative and, eventually, quantitative studies. Since an infrared spectrum is a mathematical function, one can therefore calculate and determine the slope of such function by taking the derivative. The main purpose of obtaining the derivatives is to emphasize weak spectral features which are buried beneath dominant spectral features. In particular, the bottom of the downward pointing feature pinpoints the exact wave number of the maximum absorbance of the peak. These wave numbers then can be used in turn to estimate the number of overlapping bands in the composite and to locate their possible peak positions.

Using FT-IR spectrometers, it is possible to apply what is known as Fourier derivation. During this process, the spectrum is first transformed into an interferogram. It is then multiplied by an appropriate weighting function and finally it is "re-transformed" to give the derivative. This technique provides more sensitivity than conventional derivatization.

It has to be noted that sample handling errors, spectral fringes, baseline shifts, batch to batch variations, the presence of non-diagnostic debris and all other factors are adversely affect discrimination.

In order to improve the resolution, it is preferred to measure several samples of the same cell type processed in the same manner and to standardize the spectra obtained. Standardization, Fourier transformation and derivation are carried by methods known to the person skilled in the art. Preferably all calculations are made by computer. In accordance with the invention, derivatives of the second and, optionally, a higher order may be used. According to a preferred embodiment of the invention, the multiple derivative used for the identification of deviations is a second derivative.

Cultivation in-vitro requires on the one hand that only the desired cell types are cultivated from any tissue biopsates obtained from the patient and, on the other hand, that only this cell type is transplanted into the patient. To achieve this, strict control of the preparation from the starting material, of the cell culture and of the finished cell product to be transplanted is necessary.

An essential problem encountered both in the recovery of the biopsates and in culture management is the fact that cells in a tissue are often not present in their pure form, but in the form of a mixture of different cell types. In addition to chondrocytes or cartilage cells, cartilage, for example, contains fibroblasts which are also found in most of the other tissues. Fibroblasts constitute an undesirable contamination of cell cultures insofar, as they usually grow faster than the desirable specific, well or fully differentiated cells. As a result, they can form the majority of the cells in the cultures after a very short time so that this culture no longer corresponds to the desired tissue type. According to the invention, preferably the biological sample such as biological cells and/or microorganisms is used in a purified form. In a further preferred embodiment, the sample comprising biological cells and/or microorganisms according to the present invention is substantially free of non-diagnostic debris.

In another aspect the invention relates to a method for in-vitro analysis of biological and/or microorganisms' donor individuals. This method is useful to determine cells from a specific donor individual in a group consisting of cells of a specific cell type, wherein the cells of this cell type origin from different donor individuals. In general this applies for all kind of cells. For instance, each of the cell types chondrocytes, oesteocytes, periosteal cells, stomach cells, epithelial cells, fibroblasts, melanocytes and/or muscles cells form a kind of cluster having specific subgroups within the cluster. Now it has surprisingly been found that within one subgroup comprising specific cells types from different donor individuals, the donor individuals can be determined. Each individual has a specific pattern based on different intensities at selected wavelengths which can be determined by generating the first or multiple, preferably the second, derivative transformation of the FT-IR spectrum of the method as described in the first embodiment. The selected wavelengths include the range of 4000 $cm^{-1}$ to 400 $cm^{-1}$, preferably 1500 $cm^{-1}$ to 700 $cm^{-1}$, and most preferably 1300 $cm^{-1}$ to 900 $cm^{-1}$.

Therefore, the invention also relates to a method for in-vitro analysis of biological cells' and/or microorganisms' donor individual or individuals. Said method comprising the steps of:
(a) projecting infrared radiation on a sample of biological cells from different donor individuals, said radiation including a selected number of wavelengths;
(b) recording the spectral characteristics after interaction with said sample;
(c) deriving a Fourier transform infrared spectrum (FT-IR) from the collected spectral characteristics;
(d) generating the first or multiple derivative transformation of the FT-IR spectrum suitable for analysis in a computer;
(e) comparing said derivative with the derivative of a reference FT-IR spectrum determined earlier of each donor individual;
(f) identifying deviations of said derivative from said reference derivative; and
(g) providing an analysis of said characteristics based on the presence of said deviations.

This is especially useful in the field of transplantation/graft and tissue engineering. In case various culture flasks are mixed up then it would be possible to determine the cells donor individual.

Water absorbs strongly in the mid-infrared region and contributes to changes in intensity at several frequencies. Thus, in biological objects the most interesting resonance frequencies of the C=N, C=O, N—H or O—H vibrations are often hidden by the strong IR absorption of the water at around 3400 and 1600 $cm^{-1}$. Experiments in aqueous systems are therefore possible only with very thin water layers and with high concentration of the molecules of interest. In order to reduce the influence of water on the obtained IR-spectra, usually, the samples are dried before use and a multiscan regime with high resolution is applied.

According to the method of the invention, a sample of interest is taken and processed in a known way to allow for recording of IR spectra. One common way to prepare a cell sample is to coat a cell suspension onto a suitable substrate and to dry said cell suspension at a temperature of 20° C. to 25° C. (room temperature or ambient temperature). That example of a preparation technique allows for easy transportation of the sample to the IR laboratory as well as for subsequent easy handling and storage.

As a rule, the method of the invention is carried out on cells in suspension. For this purpose, the cells may either be removed directly from the tissue formation and subjected to determination according to the invention. Alternatively, the cells may first be cultivated and aliquots of the culture examined by means of the method of the invention, optionally after trypsination for detaching the cultivated cells from their substrate. Optionally, aliquots of the sample solution may first be frozen and then thawed for testing. The amount of substance required for IR spectra can be very small. Depending on the conditions set, such as spectroscopy with or without beam focusing, sample amount in the mg to ng ranges can be used. As a rule, 10 to 500 µl of the cell suspension at cell counts of $1 \times 10^3$ to $2 \times 10^5$ cells per ml are sufficient for the determination. The cells may be dissolved in a suitable solvent, such as water, culture medium, buffer, physiological saline, etc. It is not necessary to separate additives such as serum albumins, especially human serum etc., from this solvent. However, the best results were achieved by investigating pure cells. In case of any additives a reference FT-IR spectrum can be optionally determined earlier in order to determine the deviations properly. In this case also a FT-IR spectrum of one or more additives can be recorded in order to set the final spectrum in correlation to the earlier determined spectrum of the additives.

The suspension is coated onto a carrier suitable for the IR measurement. After coating, the solvent is preferably evaporated so that a dry sample is obtained. According to the invention, this sample is irradiated with IR light and the adsorption spectrum recorded in accordance with the method of the invention. Preferably, at least three, generally three to five parallel measurements are taken on one sample. The carrier may consist of any material suitable for IR, preferably glass, silicon or silver mirror. For example, suitable carriers are described in the German patent application DE 100 60 560.

In a further preferred embodiment, the preparation procedure of a sample according to the invention comprises:
(i) coating a suspension of the cells to be determined onto a suitable carrier; and
(ii) evaporating the solvent from the suspension in order to obtain a dry sample.

According to a further preferred embodiment, the cell sample is dried prior to producing the infrared spectra in step (a).

Once in the lab, the IR radiation, including a selected number of wavelengths, is passed through the sample and the IR spectra are recorded and compared with the reference spectrum. The presence or absence of a certain graphical elements (IR bands) in comparison to the reference spectrum is used for analyzing the sample.

In step (e) of the method of the invention, the derivatives of the FT-IR spectra obtained from the sample are compared with the same derivative of a reference FT-IR spectrum obtained earlier. For this comparison, according to a further preferred embodiment of the present invention, the reference spectra are obtained either starting from pure cultures of the cell type/microorganism type of interest and/or starting from known mixed cultures of the cell and/or microorganism type of interest with one or more additional cell and/or microorganism types. Preferably, the reference spectra are prepared starting from pure cultures of the cell type of interest in various solvents. One of these solvents is identical with the solvent of the sample.

If desired, the reference spectra may also be prepared starting from mixed cultures of the cell type of interest with one or more other cell types. Examples are mixed cultures of the desired cells and, for example, the ubiquitous contaminating fibroblasts. By a comparison with such mixed reference spectra, the method of the invention makes it possible to determine the contamination of a cell culture or sample and, optionally, the ratio between the desired cell type and the contaminating cell type.

According to the invention, infrared light of a suitable wavelength is used to irradiate the cells. As a rule, any kind of infrared light may be used, e.g., light in the wavelength range from 760 nm to 500 μm. Infrared light of the near, medium (mid) or far IR range is suitable. Preferably, infrared light having a wavelength from 760 nm to 2,000 nm, and most preferably infrared light of the medium range from 800 nm to 1,500 nm, is used.

One or several spectral regions can be selected by visual inspection of spectra, e.g., by selecting the ranges that show the strongest and most characteristic changes as compared to the reference spectra, or by a generally known multivariate method for selecting spectral characteristics.

In a further preferred embodiment, the infrared spectrum is taken in the mid-infrared spectral region between 400 and 4000 cm$^{-1}$, preferably between 700 and 1500 cm$^{-1}$, most preferably between 800 and 1400 cm$^{-1}$, in particular between 900 and 1300 cm$^{-1}$. It was found that the marked spectral differences between the sample spectrum and reference spectrum were detected in the range from 900 to 1200 cm$^{-1}$, and that this range is particularly suitable for the analysis.

There are spectral changes due to differentiation in the protein Amide I band (1700-1600 cm$^{-1}$) and in the nucleic acid absorption region (1050-850 cm$^{-1}$) indicated that RNA translation was taking place and the specific proteins were produced, reflecting the appearance of a new phenotype. These spectral changes can be detected by the shift of a band of interest.

In bio-molecules, the interesting resonance frequencies responsible for the deviation of the absorbance spectra of the cells are C=N, C=O (Amide I), N—H (Amide II) or O—H vibrations.

The term "deviation" or "spectra deviation" refers to a difference between spectra or their derivatives of the reference sample and analyzing sample.

Positions of the amide bands depending on the secondary structure of the protein or peptide are shown below:

| conformation | Vibration frequency, ν (cm$^{-1}$) | | |
| --- | --- | --- | --- |
| | Amide A (N—H stretch) | Amide I (C=O stretch) | Amide II (N—H deformation) |
| α-helix | 3290-3300 | 1648-1660 | 1540-1550 |
| β-sheet | 3280-3300 | 1625-1640 (strong) 1690 (weak) | 1520-1530 |
| β-turns | | 1660-1685 | |
| Random coil (unordered, non-hydrogen bonded) | 3250 | 1625-1660 | 1520-1545 |
| 3$_{10}$-helix | | 1660-1670 | |
| Aggregated strands | | 1610-1628 | |

The deviations of the absorption spectra of the cells as well as their derivatives are due to changes of the phosphate group PO$_2^-$ in phosphodiesters of nucleic acid can be analyzed at following frequencies: vs PO$_2^-$ (1080 cm$^{-1}$) and vas PO$_2^-$ (1245 cm$^{-1}$).

The physical parameters such as spectral resolution and number of average spectra can be varied within the typical ranges in IR spectroscopy. When determine the parameters for obtaining the spectra and preparing the sample, identical parameters have to be selected for all measurements including reference measurements. It is very important that all parameters for reference and sample measurements are identical. In a further preferred embodiment, the spectral resolution is between 2 cm$^{-1}$ and 10 cm$^{-1}$, preferably is between 4 cm$^{-1}$ and 8 cm$^{-1}$, and for each spectrum 16 to 120 scans, preferably 32 to 64 scans are taken and co-added. In general, the spectra are normalized by setting the minimum absorbance at 0.0 and the maximum absorbance at 1.0 in the frequency region between 400 and 4000 cm$^{-1}$. However, in some embodiments the techniques of the invention are practiced without normalizing the spectra. In a further preferred embodiment, the spectral data is smoothed and/or derivatized. Thus, according to one preferred embodiment, the data is first smoothed and then derivatized. According to another preferred embodiment, the data is first derivatized then smoothed.

Narrower spectral regions even in near (NIR) infrared range from 4000 cm$^{-1}$ to 10,000 cm$^{-1}$ can also provide successful information, since NIR-spectra consist of overtone and combinations based on the fundamental vibrations seen in the mid-IR. Thus, NIR is expected to contain the same information which is useful in making the mid-IR analysis.

The comparison of the absorption data and the reference absorption spectra is made using any technique or instrumentation known to those skilled in the art for comparing spectral data sets. In a further preferred embodiment, comparison of the infrared absorption data for the sample and the data for the reference set utilizes principal component analysis in the frequency region from 400 to 4000 cm$^{-1}$, especially preferred the comparison is conducted in the range from 700 to 1500 cm$^{-1}$, most preferably between 800 and 1400 cm$^{-1}$, in particular between 900 and 1300 cm$^{-1}$.

According to the method of the invention, a sample of interest may be irradiated using any known way to allow for recording of IR spectra. In a further preferred embodiment of the present invention, the infrared radiation in step (a) interacts with the sample, and the characteristically altered radiation is detected in one of a transmission/absorption or attenuated total reflection setup.

The present invention relates to a method for the in-vitro analysis of biological cells and/or microorganisms which may be carried out in a simple and, preferably, automated manner, produces results rapidly and permits the reliable determination/detecting of structural changes between a biological sample and a reference sample.

Classical methods for the analysis of biological cells and/ or micro-organisms such as morphological and histological methods and the genetic determination by means of PCR typically require up to 48 hours or longer until concrete results may be obtained. On the other hand, cells recovered when tissue samples are taken from a patient must be transferred into a culture immediately to keep the cells viable. Likewise, the transplant/graft should be re-introduced into the patient as soon as possible, provided the desired cell count has been reached. In addition, monitoring or typification of the cell material to be transplanted should be carried out within a short period of time before and as close to transplantation rather than already known methods of the prior art, e.g., PCR, specific marker, NMR-spectroscopy methods, where the analyzing interval of few days, e.g., of two days, is applicable.

The structural difference between the sample and the reference sample can arise from any process known to cause structural changes in the sample, e.g., changes in a chemical structure, functional group or molecular sequence orientation. Different biological cell types and/or microorganisms can possess inherent structural/chemical differences which are spectroscopically accessible. The spectroscopic changes observed relate to changes in the concentration and conformational orientation of functional groups associated with proteins, lipids, nucleic acids and carbohydrates. In a further preferred embodiment of the invention, the deviations according to steps (e) and (f) arise from the structural difference of the sample. Preferably, the chemical differences arise as a result of a disease state in the cell or tissue under study, e.g., cancer, dysplasia, diabetes, hypertrophy, etc. The disease state is one caused by a pathogen, e.g., bacteria or virus, or can arise due to a genetic anomaly. Chemical differences in cells may also arise due to a culture condition, e.g., a cell medium, upon the cell.

It is well known that as cell medium a solution comprising serum as a fluid component obtained upon separating whole blood into its solid and liquid components, containing antibodies, electrolytes and soluble proteins, is used. Therefore depending on the culture conditions, such as cell medium, biological cells may grow with different degree of modification, such as e.g., degree of differentiation. Thus, it is very important to analyze the culture conditions such as a concentration of serum in a solution used as a cell medium, pH, type of electrolyte, organic and inorganic impurities. According to a further preferred embodiment, the method according to the present invention further includes a step of analyzing which medium conditions were applied to the biological cells or microorganisms based on said deviations. For instance, the invention also relates to a method for in-vitro analysis of biological cells' culture conditions, wherein the serum content of the used culture medium, e.g., whether the cells were cultured in a medium comprising 5% or 10% serum, is analyzed.

The method of the invention permits the analysis of biological cells and/or microorganisms. According to the invention, the biological cells, preferably mammal cells, most preferably human cells, are selected from the group consisting of: (i) blood cells, e.g. erythrocytes, reticulocytes, leukocytes, thrombocytes, megakaryocytes, mast cells, dendritic cells; (ii) immune cells, e.g. lymphoid cells: B cells, T cells (cytotoxic T cells, natural killer T cells, regulatory T cells, T helper cells), natural killer cells; myeloid cells: granulocytes (basophil granulocytes, eosinophil granulocytes, neutrophil granulocytes/hypersegmented neutrophil) monocytes/macrophages; (iii) endocrine system cells: thyroid cells (thyroid epithelial cells, parafollicular cells), parathyroid cells (parathyroid chief cells, oxyphil cells), adrenal cells (chromaffin cells), pineal cells (pinealocyte); (iv) nervous system cells: e.g. glial cells: glioblasts (astrocyte, oligodendrocyte), microglia, magnocellular neurose-cretory cells, Stellate cells, Boettcher cells, pituitary cells (gonadotrope, corticotrope, thyrotrope, somatotrope, lactotroph cells); (v) respiratory system cells, e.g. pneumocytes (Type I pneumocytes, Type II pneumocytes), Clara cells, Goblet cells, Alveolar macrophages; (vi) circulatory system cells, e.g. myocardiocytes, pericytes; (vii) digestive system cells, e.g. stomach cells (gastric chief cells, parietal cells), Goblet cells, Paneth cells, G cells, D cells, ECL cells, I cells, K cells, S cells, enteroendocrine cells, enterochromaffin cells, APUD cells, liver cells (hepatocytes, Kupffer cells); (viii) cartilage, bone and muscle cells: bone cells: osteoblasts, osteocytes, osteoclasts, teeth cells (cementoblasts, ameloblasts), cartilage cells: chondroblasts, chondrocytes, (ix) skin and hair cells: trichocytes, keratinocytes, melanocytes (Nevus cells); (x) muscle cells: myocytes, other cells: adipocytes, fibroblasts, tendon cells; (xi) urinary system cells, e.g. podocytes, juxtaglomerular cells, intraglomerular mesangial cells, extraglomerular mesangial cells, kidney proximal tubule brush border cells, macula densa cells; and (xii) reproductive system cells, e.g., male cells (spermatozoon, Sertoli cells, Leydig cells) and female cells (ovum cells).

Preferably the human cells are selected from the group consisting of: chondrocytes, osteocytes, periosteal cells, stomach cells, epithelial cells fibroblasts, melanocytes and muscle cells.

In mixed cultures, fibroblasts are usually present as an additional cell type. According to a further preferred embodiment of the invention, the microorganisms are selected from bacteria, fungi, archaea, protists, viruses and animals, such as e.g., plankton and planarian and mixture thereof.

The method of the invention may be used for in-vitro analysis, e.g., examination, determination, classification, identification, typification, differentiation, distinguishing, monitoring, quantification, diagnosis and/or as a status check.

According to a second aspect, the present invention thus provides an apparatus for in-vitro analysis of biological cells and/or microorganisms characteristics selected from the group consisting of: degree of differentiation, cell types, donor individuals, culture conditions, purity, lack of natural characteristic, or additional characteristics in comparison to natural characteristics, comprising:

a sample-receiving device for a suspension of biological cells and/or microorganisms;

a means for irradiating a sample of biological cells and/or microorganisms with infrared light and a means for recording the absorption spectrum obtained;

a means for carrying out a Fourier transformation of the absorption spectrum obtained into a FT-IR spectrum;

a means for calculating the first, and, optionally, multiple derivatives of the FT-IR spectrum; and a means for comparing the derivative(s) from the step (d) in a preselected wave number range with the same derivative(s) of reference FT-IR spectra prepared earlier and stored in the apparatus.

Apparatuses according to the features (a) to (d) are known in the prior art. In this respect, reference is made to the German patent specifications DE 199 49 953 (corresponds to U.S. Pat. No. 6,493,080 B1) or DE 199 40 981, the disclosures of which are incorporated herein by reference in their entirety.

The apparatuses of the invention are characterized in that the reference spectra are already stored in the apparatus and an automatic comparison of the desired derivatives with the derivatives of the reference FT-IR spectra is therefore possible.

According to another aspect, the present invention provides the use of a method and an apparatus according to the above described method in the field of transplantation/graft and tissue engineering, clinical medicine, pharmaceutical industry, quality control and/or drug safety. Also the use of the method and apparatus allows for rapid and accurate early diagnosis, frequently pointing out to the initial stage of the disorder when no clinical manifestations are yet observed due to lack or addition of natural characteristics in comparison to the natural characteristics of the investigated biological cells and/or microorganisms.

The method of the invention can also be used to monitor the course of a reproduction or differentiation of cells which is progressing, resolving or in steady-state. Therefore, the quality control as well as purity control of the starting material and the finished product is of crucial importance because the smallest amount of any impurities may significantly (negative) influence the treating of a patient. According to a preferred embodiment, the method or the apparatus of the present invention are used for pharmaceutical quality control and drug safety of biological cells and/or microorganisms.

Especially transplants/grafts, namely parts of a tissue or an organ that are transported from another living being into a patient are the most important field of clinical medicine. In recent years, the medical field has developed techniques for examination and characterization of cells used in the transplantation/graft medicine. In a further preferred embodiment, the method or the apparatus of the present invention are used to analyze purity of biological cells used in a transplant/graft.

For example, as the reproduction/differentiation or disease state progresses, the spectral data acquired from the cells of interest will diverge more sharply, over time, from the spectral data acquired from reference cells. In contrast, as a disease state resolves, the spectral data from the cells of interest will converge on the spectral data acquired from the reference cells. Also within the scope of the invention is the study of cells and tissue in which the disease state is in remission. The detectable structural changes in the cells are induced by environmental conditions such as for example a composition of a solution or variation of concentration of the solution components. In a further preferred embodiment, the method or apparatus of the present invention are used for monitoring changes in cellular types over time, degree of differentiation or culture conditions.

In other embodiments, the chemical differences, or the changes in the chemical differences over time, are due to the treatment or progress of a disease state. The treatment can take any form known to those of skill in the art. For example, the effects of administration of pharmaceutical agents can be monitored by the method according to the invention, i.e. the agents, the administration of which is caused by detectable structural/chemical changes. In a further preferred embodiment, the method or apparatus of the present invention are used for monitoring diseases by analyzing lack of natural characteristics or additional characteristics in comparison to natural characteristics.

Another advantage is that the method of the present invention allows for a rapid analysis or differentiation between a number of likely medical conditions, all of them presenting with similar clinical symptoms. This method has real advantages because it gives a chance to simultaneously diagnose different organs pathology in contrast to some well known diagnostic methods which can be used for diagnostic diseases for only one organ e.g. heart, brain or stomach. According to the present invention, the methods or the systems are used to diagnose diverse diseases. Diseases may be are caused by activation or deactivation of specific genregion resulting in over-expression or suppression of proteins as well as mutations; i.e., a lack of natural characteristic or an additional characteristic in comparison to the natural characteristics. These diseases may caused by viral or bacterial infection, prion diseases, e.g., BSE, diabetes and cancer. Preferably the viral diseases are selected from HIV or HPV infections.

The method can be used in medicine, pharmacology and parasitology. It can also be helpful for diagnostics of some oncology and infection diseases such as HIV or hepatitis B on the earliest stage, when no clinical manifestations and antibodies are present. Moreover, the method can be used in different branches of biology, such as zoology, entomology, ichthyology, ornithology and botany.

Figure 1:
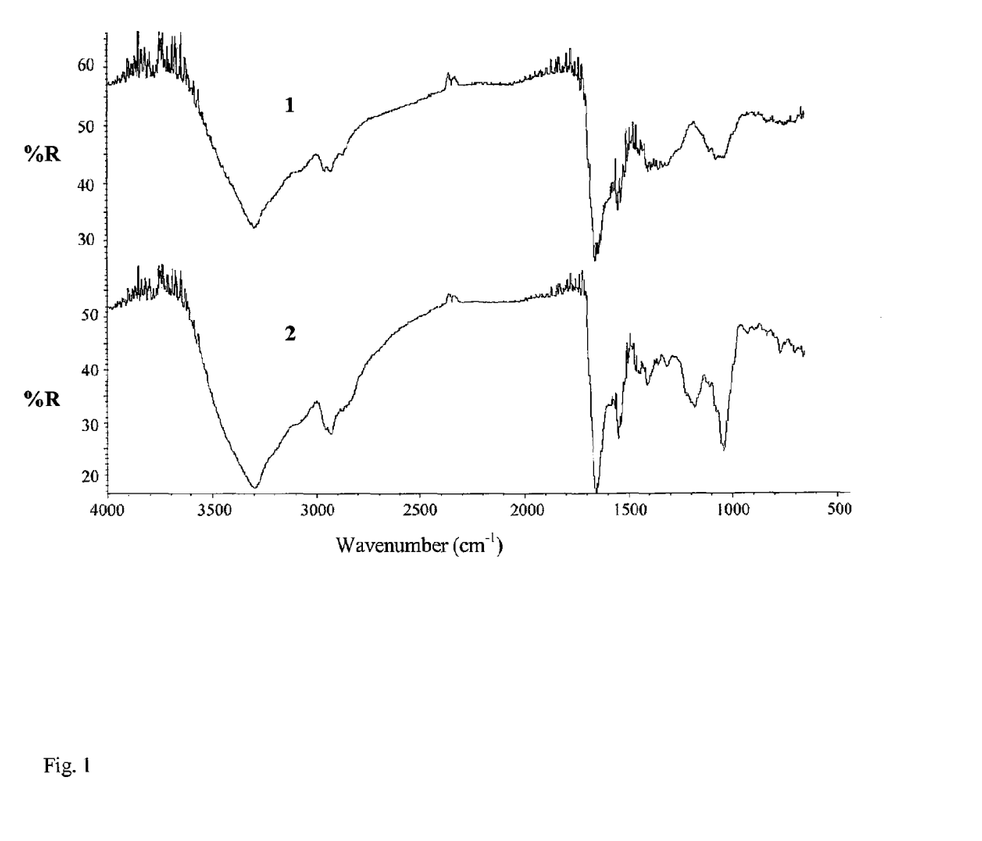
FIG. 1 shows FT-IR spectra of chondrocytes (1) and stomach cancer cells (2).

The invention will now be described in more detail by way of examples and with references to the accompanying figures:

FIG. 1 shows FT-IR spectra of chondrocytes (1) and stomach cancer cells (2).

Figure 2:
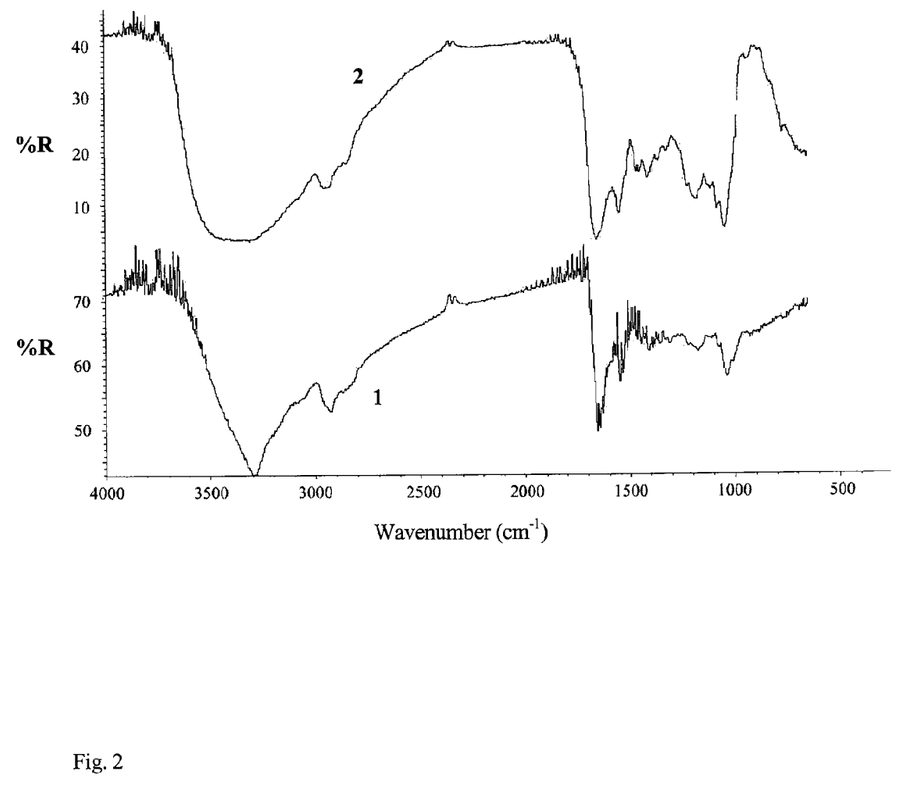
FIG. 2 shows FT-IR spectra of chondrocytes measured as a single cell (1) and as a cell agglomerate (2).

FIG. 2 shows FT-IR spectra of chondrocytes measured as a single cell (1) and as a cell agglomerate (2).

Figure 3:
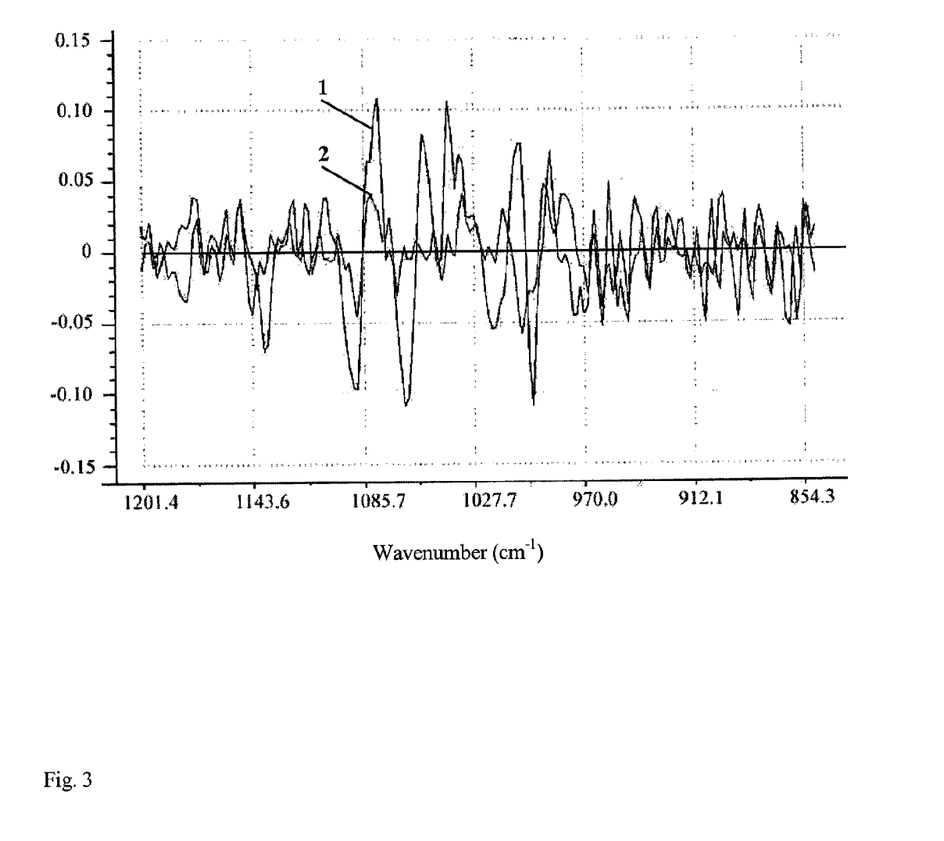
FIG. 3 shows the second derivative of the spectra from FIG. 1 in the wave number range from 850 $cm^{-1}$ to 1200 $cm^{-1}$: chondrocytes (1) and stomach cancer cells (2).

FIG. 3 shows the second derivative of the spectra from FIG. 1 in the wave number range from 850 $cm^{-1}$ to 1200 $cm^{-1}$: chondrocytes (1) and stomach cancer cells (2).

FIG. 1 shows that there is significant difference in the FT-IR spectra of chondrocytes (1) and stomach cancer cells (2), especially in the finger print region between 900 and 1500 $cm^{-1}$. The specific/characteristic IR bands of this region are used for the identification and further classification of said biological objects.

FIG. 2 shows FT-IR spectra of chondrocytes measured as a single cell (1) (non-aggregated state) and as a cell agglomerate (2) (aggregated state). The broad complex band of the hydroxyl vOH vibration region at about 3300 $cm^{-1}$ corresponding to spectrum (2) is attributed to combined effect of differently associated hydroxyl groups, i.e. hydrogen bonding between hydroxyl and hydroxyl/carbonyl groups of different strength and hydrogen bonding of water molecules. The comparison of spectrum (1) and (2) clearly demonstrates this effect. The broad band at about 1550-1700 $cm^{-1}$ corresponds to combined vibrations of Amide I (C=O stretch) and Amide II (N—H deformation) bands as well as deformation vibration of water molecule.

FIG. 3 shows characteristic differences of the second derivative spectra of chondrocytes (1) and stomach cancer cells (2) in the wave number range from 850 $cm^{-1}$ to 1200 $cm^{-1}$. Accordingly, the invention uses the first derivation and/or one or more higher derivations of this spectrum for unambiguous differentiation. The second derivative of the FT-IR spectrum from FIG. 1 is shown for the range of the mean IR light in FIG. 2. FIG. 2 clearly shows that distinct and characteristic differences of the spectra are observed in the range of the second derivation. These are used to analyte the biological objects according to the present invention such as biological cells and/or microorganisms.

The invention will now be illustrated in detail with reference to the non-restrictive examples which follow:

Example 1

An infrared measuring FT-IR spectrometer Thermo Nicolet Nexus EURO was used to carry out the method of the invention. This is an IR measuring apparatus which already contains software for the measurement, evaluation—i.e. the Fourier transformation—and documentation as well as derivation of the absorption spectra recorded. The measurements were carried out in the spectral range of 4000-400 cm$^{-1}$.

Cell suspension were coated onto the individual measuring points of the silver mirror (Thermo Spectra-Tech). After coating, these suspensions were left to dry at room temperature. The measurement was taken immediately after drying in a wavelength range from 400 to 4000 cm$^{-1}$. Various parallel determinations were carried out for each sample.

Before the measurements the reference spectra of polystyrene standard (NIST standard) were recorded in order to prove working conditions of the equipment.

The spectra obtained for chondrocytes (1) and stomach cancer cells (2) are shown in FIG. 1.

FIG. 3 shows the second derivatives of the spectra from FIG. 1 in the wave number range from 850 cm$^{-1}$ to 1200 cm$^{-1}$: chondrocytes (1) and stomach cancer cells (2).

Example 2

In accordance with example 1, chondrocyte samples of a single (individual) cell and cell agglomerate just prepared were examined. The corresponding spectra are shown in FIG. 2.

Therefore, the invention provides a both simple and fast method for in-vitro analysis of biological cells and/or microorganisms characteristics selected from the group consisting of degree of differentiation, cell types, donor individuals, culture conditions, purity, lack of natural characteristic, additional characteristic in comparison to natural characteristics, and is therefore suitable for routinely checking cell preparations used in transplantation/graft medicine. One of the main reasons for that is that rapid, inexpensive analysis is possible with minimum sample amounts.

The present invention is not limited to the subject matter of the samples shown above. A person skilled in the art will recognize that modifications of the method of the invention are possible without leaving the protective scope of the application defined by the appended claims.

Example 3

In accordance with one embodiment, there is provided a method for in-vitro analysis of biological cells and/or microorganisms characteristics selected from the group consisting of: degree of differentiation, cell types, donor individuals, culture conditions, purity, lack of natural characteristic, or additional characteristics in comparison to natural characteristics. The method generally comprises the steps of:
(a) projecting infrared radiation on a sample of biological cells and/or microorganisms, said radiation including a selected number of wave-lengths;
(b) recording the spectral characteristics after interaction with said sample;
(c) deriving a Fourier transform infrared spectrum (FT-IR) from the collected spectral characteristics;
(d) generating the first or multiple derivative transformation of the FT-IR spectrum suitable for analysis in a computer;
(e) comparing said derivative with the derivative of a reference FT-IR spectrum determined earlier;
(f) identifying deviations of said derivative from said reference derivative; and
(g) providing an analysis of said characteristics based on the presence of said deviations.

What is claimed is:

1. A method for in-vitro determination of origin of biological cells, comprising:
    (a) projecting infrared radiation on a sample of biological cells from different donor individuals, said radiation including a selected number of wavelengths;
    (b) recording spectral characteristics of said sample;
    (c) deriving a Fourier transform infrared spectrum (FT-IR) from the recorded spectral characteristics;
    (d) generating a derivative transformation of the FT-IR spectrum;
    (e) comparing said derivative transformation of the FT-IR spectrum with a reference FT-IR spectrum determined earlier of each donor individual;
    (f) identifying deviations of said derivative transformation of the FT-IR spectrum from said derivative of a reference FT-IR spectrum; and
    (g) confirming or denying that the biological cells in the sample originated from each donor individual based on the presence of said deviations.

2. The method of claim 1 wherein the derivative transformation of the FT-IR spectrum is a second derivative.

3. The method of claim 1 wherein the deviations arise from structural differences of the sample.

4. The method of claim 1 wherein the selected wavelengths include the range of 4000 cm$^{-1}$ to 400 cm$^{-1}$.

5. The method of claim 1 wherein the selected wavelengths include the range of 1500 cm$^{-1}$ to 700 cm$^{-1}$.

6. The method according to claim 1 wherein the sample includes biological cells selected from the group consisting of: blood cells, immune cells, endocrine system cells, nervous system cells, respiratory system cells, circulatory system cells, digestive system cells, cartilage cells, bone cells, muscle cells, skin cells, hair cells, urinary system cells, and reproductive system cells.

7. The method of claim 1 wherein the reference FT-IR spectrum for the comparison in step (e) is prepared based on cultures of the cell type of interest and known mixed cultures of the cell type of interest with at least one additional cell type.

8. The method of claim 1 wherein the infrared radiation interacts with the sample, and the radiation is detected in one of a transmission/absorption or attenuated total reflection setup.

* * * * *